United States Patent
Honkura et al.

(10) Patent No.: US 6,302,694 B1
(45) Date of Patent: Oct. 16, 2001

(54) KEEPER FOR DENTAL MAGNETIC ATTACHMENT AND ITS REMOVAL METHOD

(75) Inventors: Yoshinobu Honkura, Aichi-ken; Kazuo Arai, Tokai; Hiroyuki Tanaka; Kazunari Kimura, both of Chita; Hiroshi Mizutani, Hino; Kenji Hiranuma, Nagoya; Hisao Takakura, Tokyo-to, all of (JP)

(73) Assignee: Aichi Steel Corporation Ltd., Tokai (JP)

( * ) Notice: Subject to any disclaimer, the term of this patent is extended or adjusted under 35 U.S.C. 154(b) by 0 days.

(21) Appl. No.: 09/615,900

(22) Filed: Jul. 13, 2000

(30) Foreign Application Priority Data

Nov. 12, 1999 (JP) .................................................. 11-322388

(51) Int. Cl.[7] .................................................. A61C 13/235
(52) U.S. Cl. .......................................... 433/189; 433/220
(58) Field of Search ..................................... 433/189, 220, 433/221

(56) References Cited

U.S. PATENT DOCUMENTS

| 4,729,736 | * | 3/1988 | Weissman | 433/221 |
| 5,316,478 | * | 5/1994 | Chalifoux | 433/221 |
| 5,755,573 | * | 5/1998 | LeBlanc | 433/153 |

FOREIGN PATENT DOCUMENTS

| 4-071551 | 3/1992 | (JP) . |
| 7-136190 | 5/1995 | (JP) . |
| 11-146886 | 6/1999 | (JP) . |
| 11-276505 | 10/1999 | (JP) . |
| 11-299807 | 11/1999 | (JP) . |
| 2000-024004 | 1/2000 | (JP) . |

* cited by examiner

Primary Examiner—John J. Wilson
(74) Attorney, Agent, or Firm—Oblon, Spivak, McClelland, Maier & Neustadt, P.C.

(57) ABSTRACT

A keeper of the dental magnetic attachment and method for removal of the keeper is disclosed wherein the keeper can be attracted by a magnetic assembly embedded in a denture base. The keeper includes a body made of soft magnetic material and a post made of non-magnetic material that is connected together at the bottom of said body of the keeper. The post has a bendable part that is connected to the body of the keeper.

4 Claims, 10 Drawing Sheets

FIG. 10    *Prior Art*
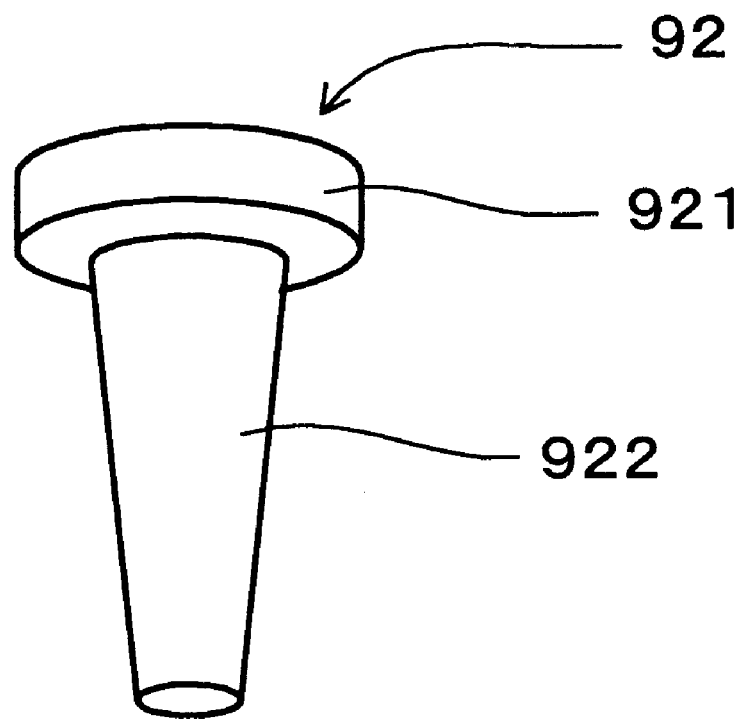

KEEPER FOR DENTAL MAGNETIC ATTACHMENT AND ITS REMOVAL METHOD

BACKGROUND OF THE INVENTION

1. Field of the Invention

The present invention relates to a keeper for dental magnetic attachments so as to fix a denture base by magnetic attraction, and a method for removing the body of the keeper from the tooth root.

2. Discussion of the Background

Dental magnetic attachments to fix denture by magnetic attraction are being developed in the dental field. A known dental magnetic attachment 9 is as shown in FIG. 8. It is composed of a magnetic assembly 91 and a keeper 92 embedded in a root cap 82 to be attracted by said magnetic assembly 91. A magnetic attractive force is generated between said keeper 92 and said magnetic assembly 91. A dental magnetic attachment having the structure mentioned above requires that keeper 92 is incorporated into the root cap 82 by a casting method.

This process in which the keeper 92 is incorporated into the root cap 82 requires precise control of casting conditions at an elevated temperature to maintain the good quality of the keeper 92. This casting process requires a lot of time and is apt to cause various problems. As a result the cost of keeper preparation is increased significantly. It also prolongs the period for medical treatment to the patients.

Therefore, at the present time, the keeper is cemented directly on the root surface with the application of advanced dental resin. In this case, the keeper 92, consisting of a body of keeper 921 and a post 922, is fabricated by machining, as shown in FIG. 9 and FIG. 10.

However the keeper 92 mentioned above faces following difficulties. First, as seen in FIG. 9 and FIG. 10, said post 922 has rather large diameter because of the limitation of machining capability. The thick post requires enlargement of the tooth canal, which makes the root fragile. Furthermore, the shape of said post 922 has no resistance against the post becoming dislodged from the root canal. Second, in the situation where the root surface is inclined against root canal, while the root cap in which a keeper is incorporated by casting can be fitted to such surface inclination, a keeper with the post 922 made by machining can not be adjusted to the inclination. Third, said keeper 92 requires a great deal of time to be removed in case of diagnosing by MRI (magnetic resonance imaging).

The keeper 92 is made of soft magnetic materials, and the material causes an undesirable influence on an MRI image. In the case where patients need to get an MRI diagnosis, both the body 921 and post 922 should be removed from the tooth root to avoid having an adverse influence on MRI image. Thus, removing of the body and post requires a great deal of time and labor.

Considering these difficulties, the present invention provides a keeper for the dental magnetic attachment which is superior in fitting to the tooth root shape, as well as being easier to be removed from tooth root when necessary. The present invention also offers the method to remove the keeper from the tooth root.

SUMMARY OF THE INVENTION

The present invention is directed to a keeper of dental magnetic attachments so as to be attracted by a magnetic assembly embedded in a denture base. This keeper includes a body made of soft magnetic material and a post made of non-magnetic material jointed together at the bottom of the body of the keeper. The post has a bendable part 21.

One of the most notable points of said keeper is that each part, namely a body of the keeper and a post jointed to said body, is of a different material, the body being soft magnetic material and the post being non-magnetic material, and that the post has the bendable part 21.

In following section the effects of present invention are described.

The keeper of the present invention has a post on the bottom, so that it can be fixed directly in the root canal with dental resin, without fabricating a costly cast root cap in which the keeper would be incorporated. In the keeper, the body of the keeper is joined together with said post. Therefore it can be fixed directly on a tooth root without using root cap but rather with the use of dental resin. Such reduces the cost and simplifies the manufacturing process by omitting a aforementioned casting process.

The post has the bendable part 21 so that the angle of the post against the body 10 of the keeper 1 can be adjusted to be desired degree. For example, in the case that the root surface is inclined against the axis of the root, said post can be adjusted with respect to the angle of the root axis by bending said bendable part. Therefore the keeper of the present invention has high adaptability to the variety of root surface conditions.

The body of the keeper is made of a different material from that of the post which is made of non-magnetic material. Thus, when MRI diagnosis is needed after embedding this keeper in the tooth root, only the body of the keeper needs to be removed before MRI diagnosis. Such therefore makes preparation for MRI diagnosis easier and requires less time than a conventional keeper, the entirety of which is made of soft magnetic material. Therefore, the present invention provides a keeper of dental magnetic attachment that is adjustable to various shape of the tooth root and relatively easy to remove.

It is preferable that said bendable part is located just under the bottom of the body of the keeper and has a smaller diameter than the other parts of the post. The smaller diameter makes the bending stiffness moderately lower and makes bending easy to accomplish. Also, a smaller diameter bendable part permits the step at the end of the part to have a bigger diameter. This step improves the anchoring effect and strengthens the stability of the keeper from detachment.

It is preferable that the diameter of said bendable part should be within a range of 0.2–0.8 mm. In case the diameter of bendable part is less than 0.2 mm, the stiffness is too low. On the other hand, in case the diameter is more than 0.8 mm, the bending stiffness becomes too high to bend.

The present invention includes a method for taking said keeper after it is fixed in the tooth root with dental resin, wherein, said body of the keeper is removed by cutting said part off from the post together with said dental resin around said body of the keeper.

One of the most notable points of the present invention is that in case of removing the keeper, said body of the keeper made of soft magnetic material is separated from the post made of non-magnetic material and that only the body of the keeper is removed.

In this situation the time required for such work is greatly reduced. Therefor, in case MRI diagnosis is needed without delay, such can be accomplished.

It is preferable to cut off the body at the bendable part. The bendable part not only has lower bending stiffness than any other part has, but also the part is easy to cut, so the work of cutting the post become much easier.

BRIEF DESCRIPTION OF THE DRAWING

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 10 a perspective view of another keeper according to the prior art.

DESCRIPTION OF THE PREFERRED EMBODIMENTS

EXAMPLE 1

The embodiments of the keeper for the dental magnetic attachment according to the present invention will now be described with reference to FIG. 1 to FIG. 10.

Figure 8:
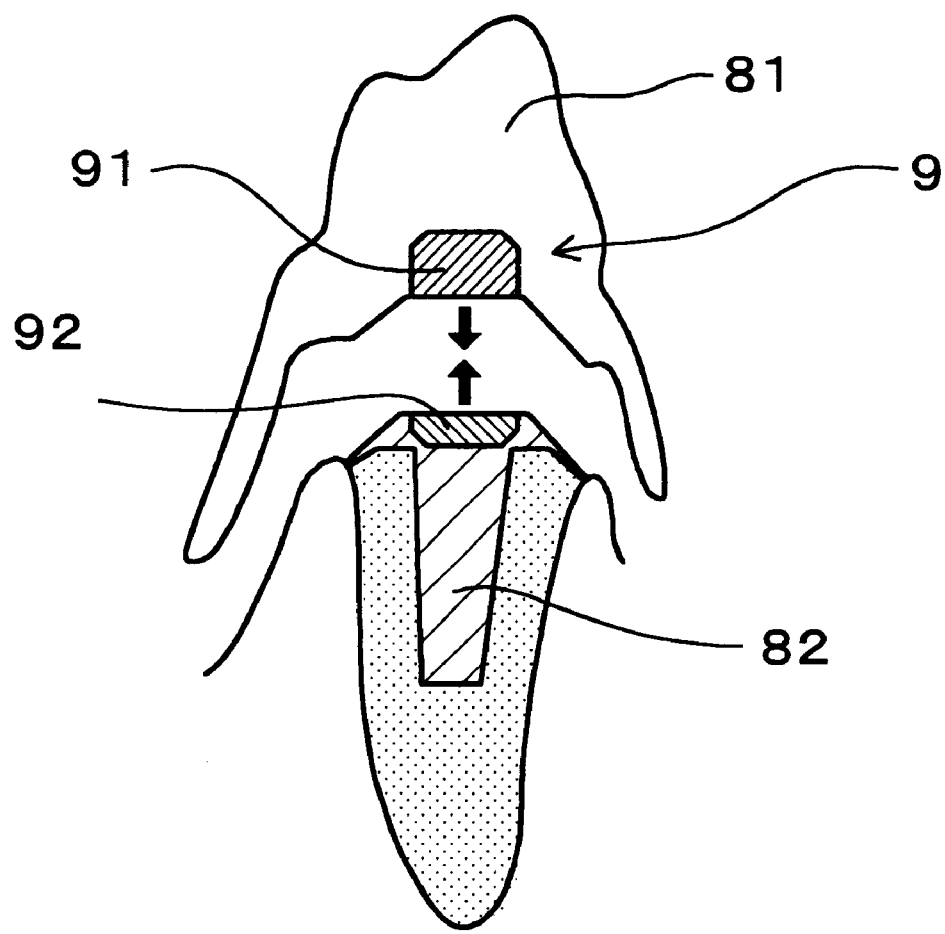
FIG. 8 an illustration of the structure of the dental magnetic attachment of the prior art.
Figure 9:
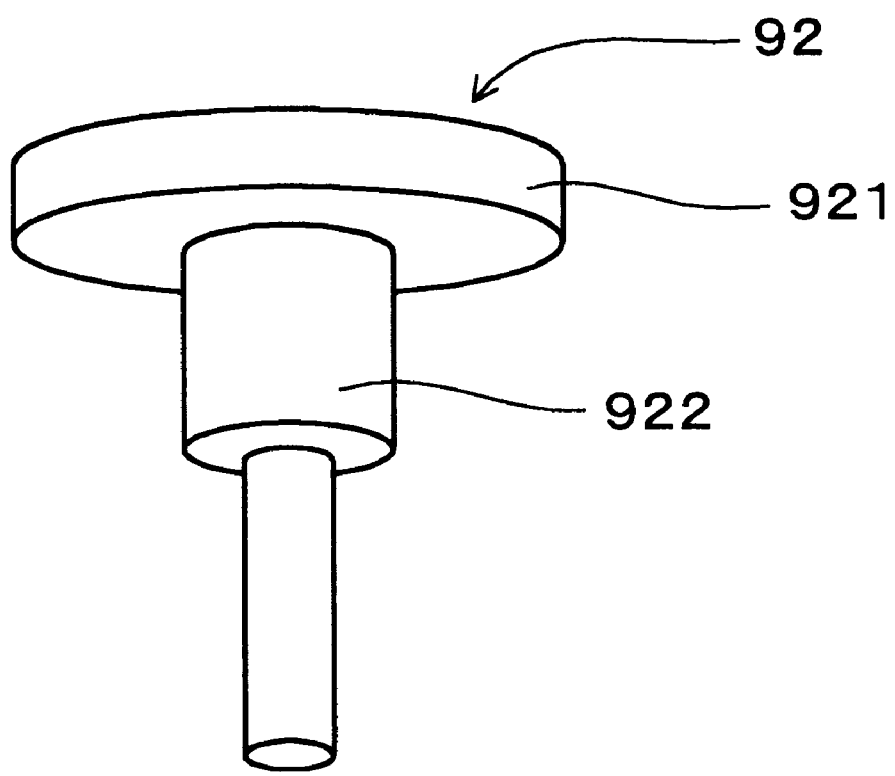
FIG. 9 a perspective view of a keeper according to the prior art.

The keeper 1 as shown in FIG. 8 is the keeper of the dental magnetic attachment so as to be attracted by the magnetic assembly 91 embedded in denture 81.

Figure 1:
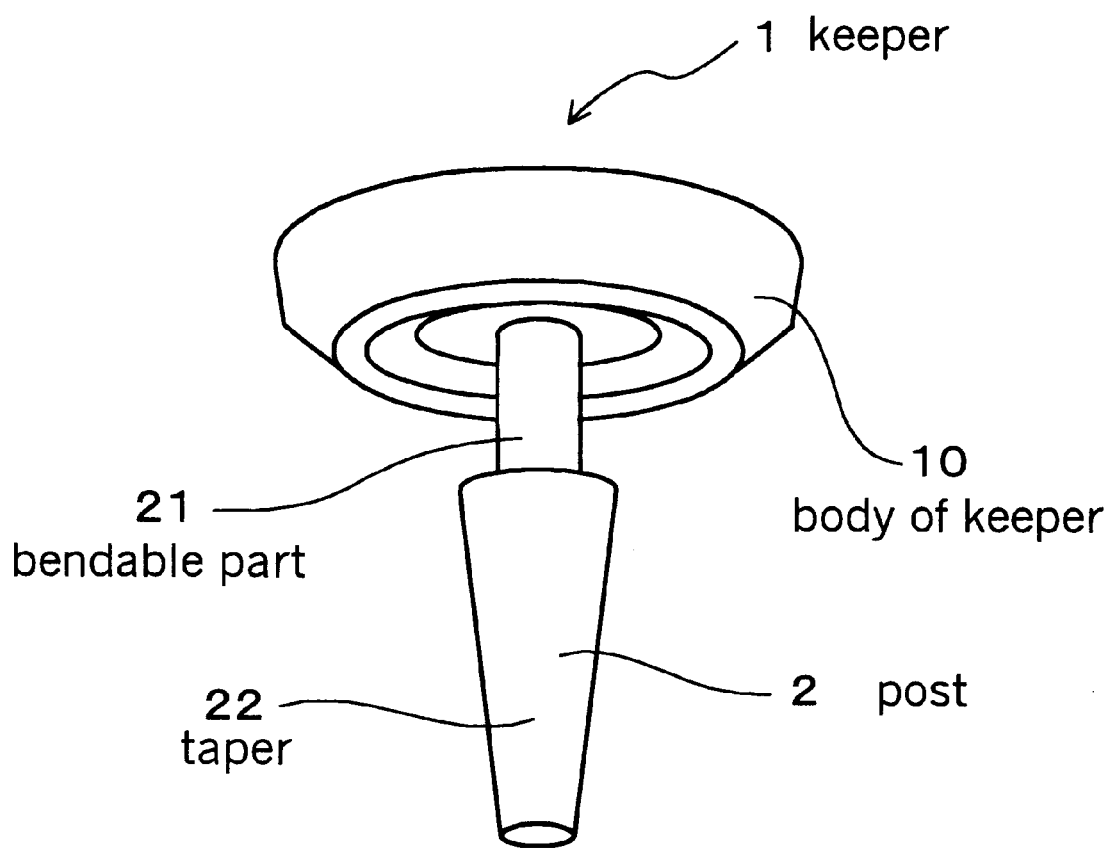
FIG. 1 is a perspective view of the first embodiment of a keeper.

The keeper 1, as shown in FIG.1, comprises a body of the keeper 10 made of soft magnetic material and a post 2 made of non-magnetic material jointed on the bottom of the said body of keeper 10. The post 2 has a bendable part 21 for bending process.

As shown in FIG. 1, the present body of the keeper 10 is made of magnetic material, Fe-19Cr-2Mo-0.2Ti soft magnetic steel, in a shape of disk.

The lateral face of the keeper body is tapered so that the diameter of the top face of the body is larger than that of the bottom face. As specific dimensions, the top diameter thereof is 3.6 mm and the thickness is about 0.7 mm. The bottom side of the body of the keeper has a hollow 15 in the center. The post 2 is jointed at the center of this hollow 15.

Figure 2:
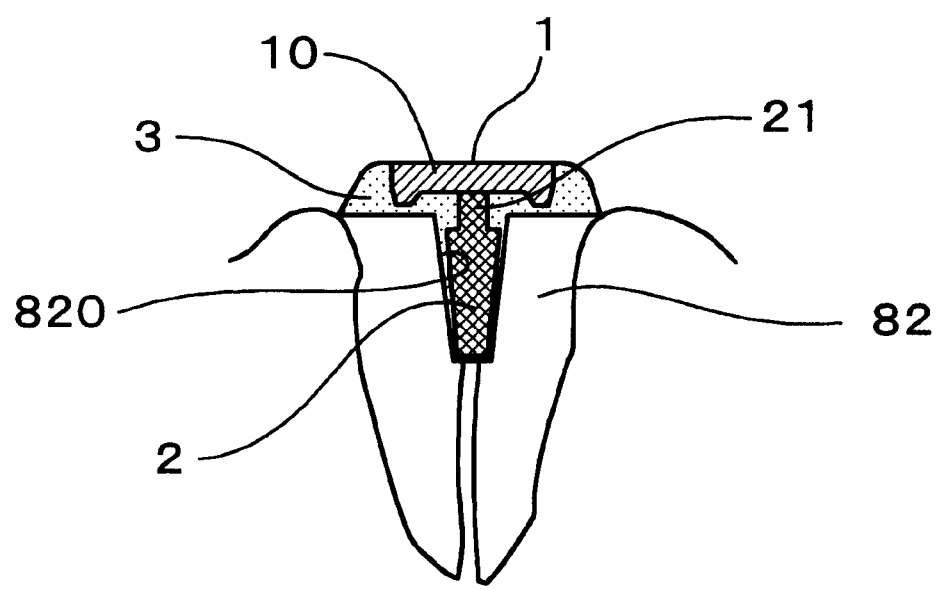
FIG. 2 is an illustration of the first embodiment of an installation of the keeper.
Figure 3:
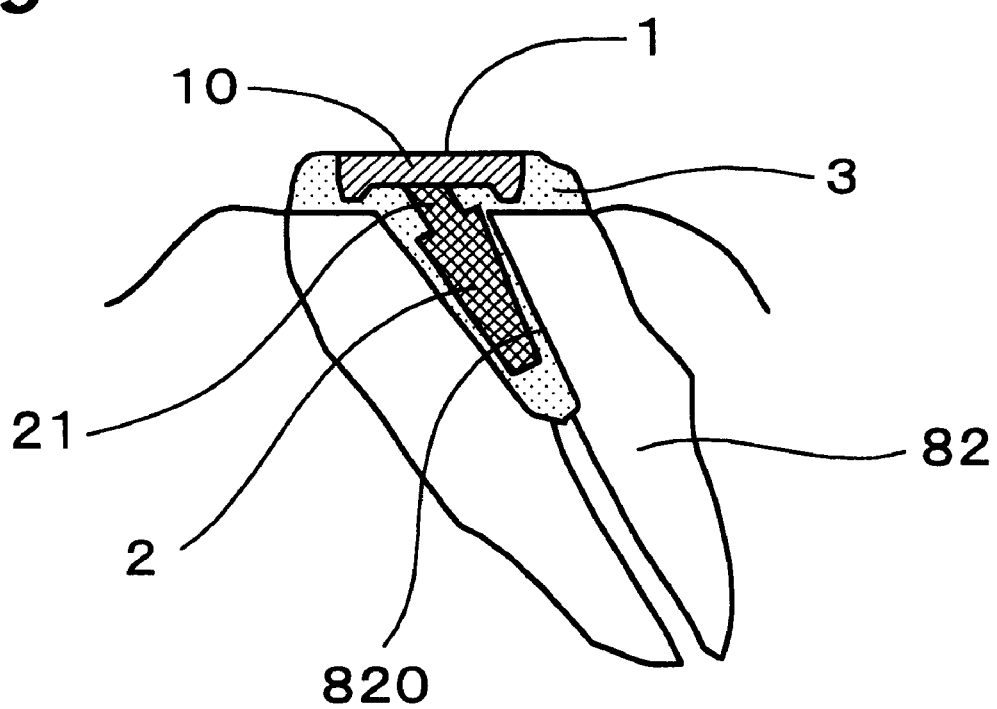
FIG. 3 is an illustration of the first embodiment of the other installation of the keeper.

The post 2 is made of non-magnetic material, SUS316 non-magnetic stainless steel specified in Japanese Industrial Standards. The post 2 has a bendable part 21 which has a smaller diameter at the connection side with the body of the keeper and taper 22 which is cone-shaped with the cut tip at the opposite side. As specific dimensions, the length of the post 2 is 7.0 mm, the top diameter of the bendable part is 0.5 mm, the largest diameter of taper 22 is 1.2 mm, and the tip diameter is 0.5 mm. FIG. 2 and FIG. 3 describe how to set the keeper 1 on a tooth root.

The cross section shown in FIG. 2 is the first example, wherein the tooth root 82 is almost vertical and the keeper is embedded in the enlarged root canal 820. In this case as shown in FIG. 2, the keeper is used as it is, in condition that the body of the keeper 10 is vertical to the post 2 without a bending. When inserting the post 2 into the root canal 820 of the tooth root 82, the keeper 1 is firmly embedded in the tooth root 82 with the dental resin 3 around the post 2 and the body of the keeper 10.

The cross section shown in FIG. 3 is the second example of the present invention, wherein tooth root 82 is inclined and the keeper 1 is embedded in the inclined root canal 820. In this case, with the bending process at the post 2, the post 2 is transformed into an inclined condition with respect to the body of the keeper 10. After that, like in the first example, upon inserting the post 2 into the root canal 820 of the tooth root 82, the keeper 1 is firmly embedded in the tooth root 82 with the dental resin 3 around the post 2 and the body of the keeper 10. Therefore, even if the tooth root 82 is inclined, the body of the keeper 10 is easily embedded in the horizontal condition.

As mentioned above, in present keeper of the dental magnetic attachment, the body of the keeper 10 is joined together with the post so it enables to embed the keeper directly to the tooth root 82 with dental resin 3 without utilizing a root cap. Therefore it enables avoiding a costly casting process, and the treatment to the patient can be completed within a day.

In addition, the post 2 has the bendable part 21. So the angle of the post 2 to the body of the keeper can be adjusted easily according to the condition. For example as shown in FIG. 3, in case that tooth root 82 is inclined and the root canal of it is also inclined, said post enables to fit to the angle of the root canal by bending the said bendable part. Therefore present invented keeper has a high adaptability to the inclination of tooth root.

In addition, the body of the keeper 10 and the post 2 are made of a different material. The post 2 is made of non-magnetic material. Therefore it enables the work to remove a keeper relatively easy as given the details below.

EXAMPLE 2

Figure 4A:
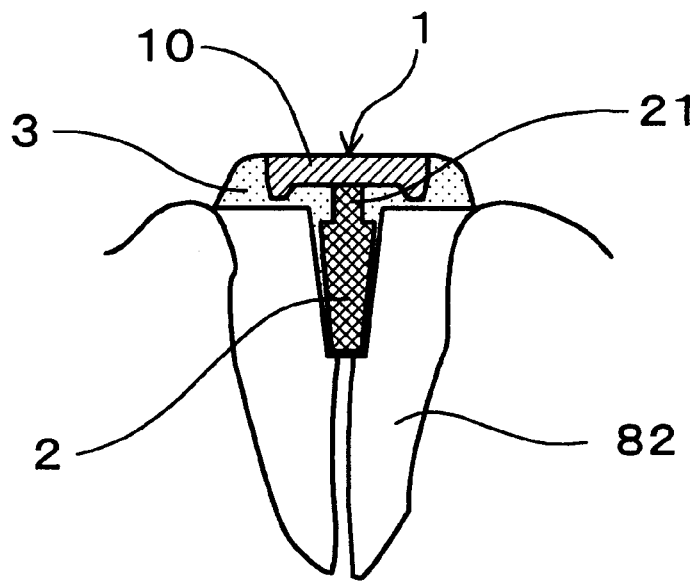
FIG. 4 is an illustration of the second embodiment of the measure to remove the keeper.
Figure 4B:
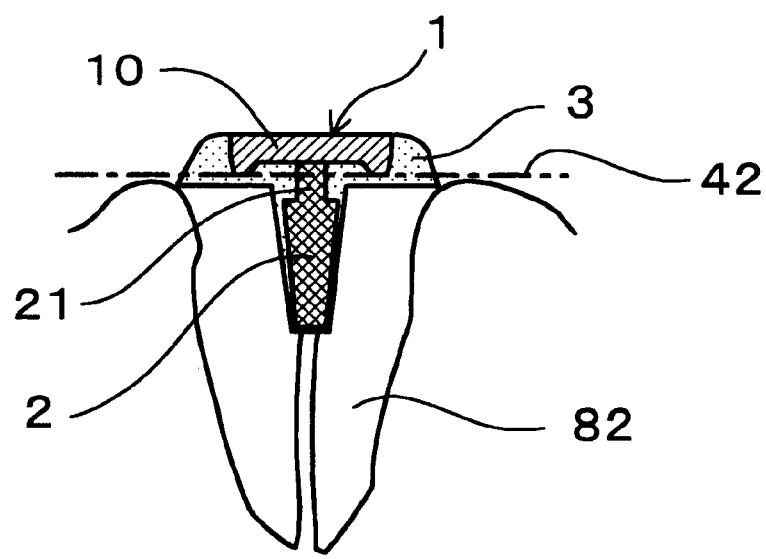
Figure 4C:
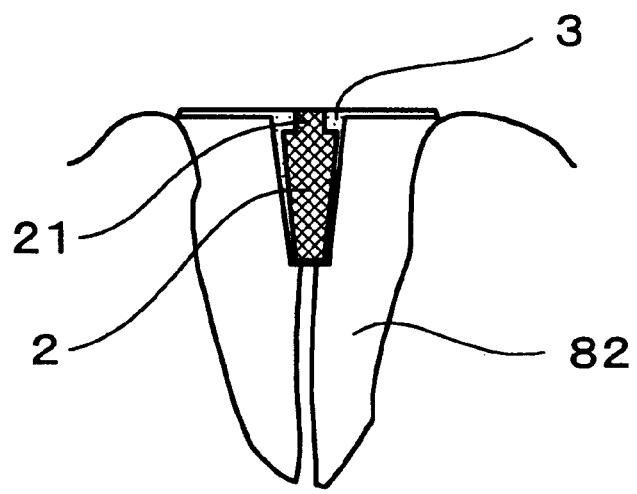

The example shown in FIGS. 4 (a)–(c) shows how to remove the keeper 1, after the said keeper of the dental magnetic attachment 1 is embedded in the tooth root 82 with the dental resin 3.

As shown in FIG. 4 (i b), by cutting the post 2 together with he dental resin 3 around the body of the keeper 10, the body of the keeper 10 is separated and taken off.

The details will be described as follows.

As shown in FIG. 2, FIG. 4 (a), in the condition wherein the keeper 1 is embedded in tooth root 82, dental resin 3 is filled between the post 2 and the canal of the tooth root 82, and around the body of the keeper 10 on the surface of the tooth root 82. In the case where MRI (magnetic resonance imaging) diagnosis is needed in this condition, the soft magnetic material of the body of the keeper 10 generates an undesirable influence and prevents an accurate MRI diagnosis. Therefore removal of this soft magnetic material is needed.

Figure 5:
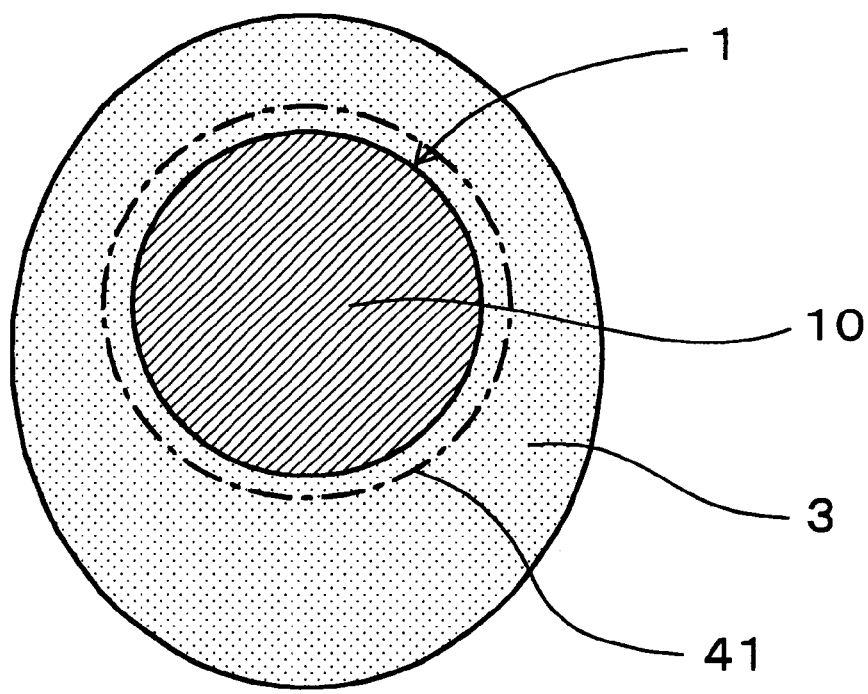
FIG. 5 is an illustration of the second embodiment of the view from above of the cutting position for removing the keeper.
Figure 6:
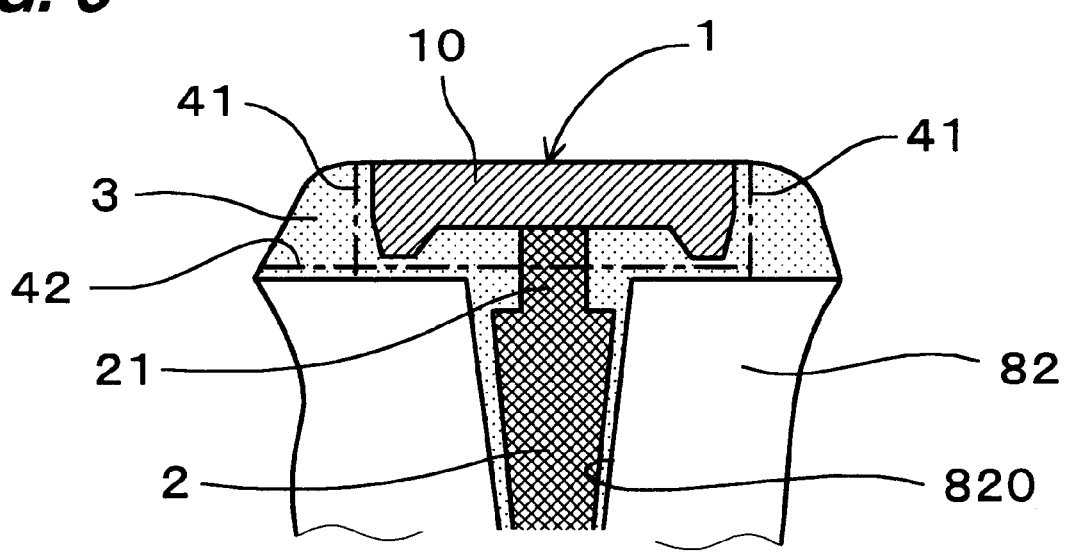
FIG. 6 is an illustration of the second embodiment of the view from vertical face of cutting position for removing the keeper.

In this example, as shown in FIG. 4 (b), a horizontal cut 42 is made to the part at a level slightly under the bottom of the body of the keeper 10. In FIG. 5 and FIG. 6, the vertical cut 41 can be given first around the body of keeper 10. In this case too, horizontal cut is given. Then the bendable part 21 of the post 2 is cut off along with the dental resin 3. In this manner, the body of the keeper 10 made of soft magnetic material can be taken off relatively easily.

Figure 7A:
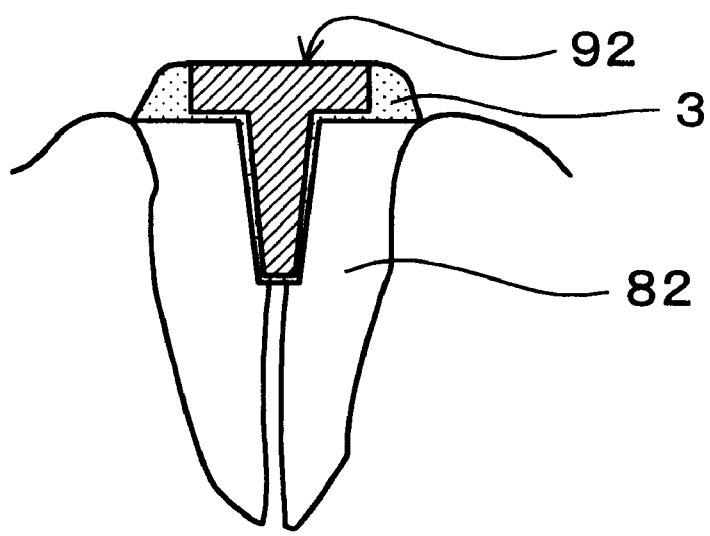
FIG. 7 an illustration of the second embodiment of the measure to remove the keeper in comparative sample.
Figure 7B:
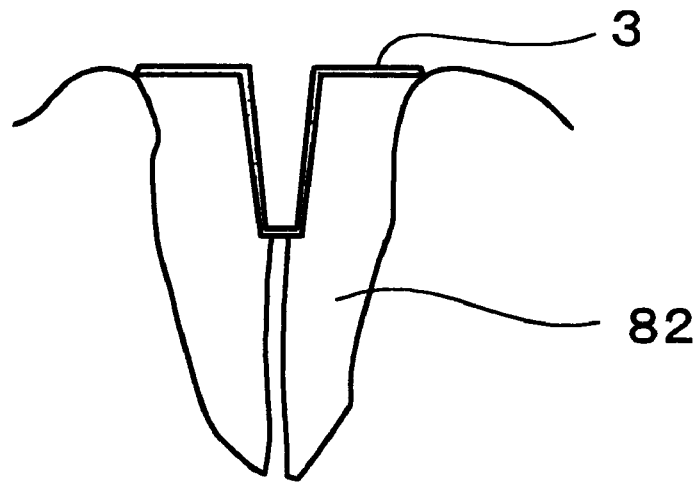

As compared with this method, the conventional method for removal of the keeper 92 with the post, the entirety of which is made of soft magnetic material as shown in FIG. 7 (*a*), is shown. In this case, as shown in FIG. 7 (*b*), not only the horizontal cut, but also a vertical hole is necessary to remove the post.

This comparison shows the advantage of the invention. Because the keeper 1 of the present invention has soft magnetic material only in the body of the keeper and the post 2 is made of non-magnetic material, only the body of the keeper 10 needs to be removed before MRI diagnosis. Therefore in case of emergent MRI diagnosis, as mentioned above, the ease of this method can make the preparation time shorter than the conventional method utilizing the prior keeper.

In addition, because of the cutting the bendable part 21 which is the thinnest part of the post 2, the cutting can be easily done.

As mentioned above, with this invention, a dental magnetic attachment is provided that has high adaptability to the inclination of the tooth root and that is relatively easy to remove and.

What is claimed is:

1. A keeper for being magnetically attracted by a dental magnetic attachment embedded in a denture base, comprising:

a keeper body made of soft magnetic material; and a post made of non-magnetic material, connected with said body at a bottom portion of said body and having a bendable part wherein said bendable part has a smaller diameter than the post and said bendable part is positioned under a bottom portion of said body.

2. A keeper for dental magnetic attachment as set forth in claim 1, wherein the diameter of the bendable part is from 0.2–0.8 mm.

3. A method of removing a keeper fixed with dental resin on a root surface of a tooth, the keeper comprising a body of soft magnetic material, which comprises:

mounting a post within a recess formed in the tooth;

interconnecting the body to the post with a bendable member having a smaller diameter than the post; and removing the keeper from the tooth by cutting off the post together with the dental resin around the body of the keeper.

4. A method of removing a keeper as claimed in claim 3, which comprises breaking the dental resin around said keeper during cutting off of the post.

\* \* \* \* \*